United States Patent [19]

Wu et al.

[11] 4,255,599

[45] Mar. 10, 1981

[54] PREPARATION OF STYRENE FROM ETHYLBENZENE

[75] Inventors: Ching-Yong Wu, Fox Chapel Borough; Thaddeus P. Kobylinski, Gibsonia; John E. Bozik, Plum Borough, all of Pa.

[73] Assignee: Gulf Research & Development Company, Pittsburgh, Pa.

[21] Appl. No.: 129,582

[22] Filed: Mar. 12, 1980

[51] Int. Cl.³ ............................................. C07C 5/333
[52] U.S. Cl. ..................................... 585/319; 585/436
[58] Field of Search ................................. 585/319, 436

[56] References Cited

U.S. PATENT DOCUMENTS

| | | | |
|---|---|---|---|
| 2,929,855 | 3/1960 | O'Connor et al. | 585/319 |
| 3,403,193 | 9/1968 | Russell | 585/319 |
| 3,665,047 | 5/1972 | Gislon et al. | 585/319 |

*Primary Examiner*—Veronica O'Keefe

[57] ABSTRACT

Ethylbenzene is converted to styrene at high selectivity in a multistage process in which ethylbenzene is oxidized to ethylbenzene hydroperoxide which is reacted with ethylene or propylene to produce a mixture of 1-phenylethanol and acetophenone which are converted to styrene.

13 Claims, No Drawings

PREPARATION OF STYRENE FROM ETHYLBENZENE

SUMMARY OF THE INVENTION

This invention relates to a multistage procedure for converting ethylbenzene to styrene.

We have discovered that ethylbenzene can be converted to styrene at an overall selectivity of 85 percent or higher in a multistage process involving ethylbenzene hydroperoxide as an intermediate product, in which each step of the process operates at high selectivity.

DETAILED DESCRIPTION OF THE INVENTION

Styrene is currently prepared by the catalytic dehydrogenation of ethylbenzene at relatively low per pass conversion using the adiabatic or isothermal cracking process. A very high temperature of about 600° C. is required for this endothermic reaction involving large quantities of high temperature steam. The capital and operating requirements for this high temperature process and for the subsequent distillative separation of the product styrene are substantial. The present process provides a method for the efficient production of styrene from ethylbenzene at significantly lower capital requirements and reduced operating costs. Although satisfactory processes are in current use for the preparation of glycols, their production as a coproduct is an added benefit.

In the first step of our process ethylbenzene is oxidized to ethylbenzene hydroperoxide as the primary product and 1-phenylethanol and acetophenone as minor coproducts by the direct oxidation using molecular oxygen. Ethylbenzene is more difficult to oxidize and is oxidized to a lower concentration of the hydroperoxide as compared with the tertiary carbon aromatic compounds such as cumene and is much less stable than these tertiary carbon hydroperoxides. For example, a 40 percent solution of ethylbenzene hydroperoxide in ethylbenzene is unstable at room temperature (20°–25° C.).

The oxidation of ethylbenzene is carried out at an elevated temperature. In this procedure ethylbenzene is placed in a reactor, preferably with between about 0.5 percent to above five weight percent of a hydroperoxide as a reaction initiator. The preferred initiator is ethylbenzene hydroperoxide, however, other hydroperoxides will initiate the reaction. The mixture is heated to a suitable reaction temperature such as between about 120° C. and about 150° C., but preferably between about 125° C. and about 140° C. An elevated temperature is also required, sufficient to maintain the ethylbenzene in solution at the temperature of reaction.

Any suitable source of molecular oxygen, such as air or pure oxygen, can be used. If the oxygen is mixed with a diluent gas, it is important that the diluent be free of any reactive contaminant gas, such as a nitrogen oxide or an oxide of sulfur, which would adversely react with one or more of the components in the reaction vessel. The partial pressure of oxygen in the reaction vessel is not critical. It is preferred that the partial pressure of oxygen in the reaction zone be at least about 10 psia. (68.9 kPa) but a partial pressure of oxygen as low as about 5 psia. (34.5 kPa) is useful. The partial pressure of oxygen can be as high as about 200 psia. (1,376 kPa) or even higher, but we prefer that the partial pressure be no greater than about 50 psia. (344 kPa).

The yield of ethylbenzene hydroperoxide and the selectivity to ethylbenzene hydroperoxide can be substantially increased in this oxidation reaction for an overall increase in process efficiency by including a minute amount of powdered barium oxide in the reaction vessel. Significant improvement in yield and selectivity to ethylbenzene hydroperoxide can be effected with as little as 0.0005 weight percent barium oxide based on the ethylbenzene with at least 0.001 weight percent being preferred. The maximum amount of barium oxide needed to obtain the desired catalytic effect is about 0.15 weight percent with a maximum amount of about 0.1 percent being preferred. It is also preferred that the reaction be carried out under substantially anhydrous conditions when barium oxide is used since water will react with the barium oxide and diminish the catalytic effect.

Depending upon reaction time and other conditions a yield of up to about 25 percent ethylbenzene hydroperoxide can be obtained at a selectivity of 90 percent or higher in the unoxidized ethylbenzene, which functions as a solvent, and more concentrated solutions can be obtained, if desired, by distilling off a portion of the ethylbenzene. Since the acetophenone and 1-phenylethanol coproduced in the first stage are ultimately converted to styrene, the overall selectivity of this first stage is essentially 100 percent. The concentration of ethylbenzene hydroperoxide in this solution can suitably be between about five and about 40 weight percent but it is preferred that it comprise between about ten and about 25 percent of the oxidized solution.

In the second stage reaction the ethylbenzene hydroperoxide in the oxidized solution is decomposed by reaction with ethylene or propylene in a homogeneous, single-phase reaction. Since ethylbenzene hydroperoxide is not significantly soluble in water, a nonaqueous reaction medium is used to obtain the homogeneous reaction system. And since te catalyst used in this reaction, osmium tetroxide, as well as the oxidized ethylbenzene hydroperoxide solution are soluble in many organic polar solvents, a polar solvent is used for this homogeneous reaction.

When this reaction for the decomposition of the ethylbenzene hydroperoxide is carried out under anhydrous conditions, 1-phenylethanol and acetophenone are produced in equimolar amounts. However, water, which is slightly soluble in the solution if present in the reaction vessel, can theoretically enter into the reaction to produce only 1-phenylethanol in the decomposition of the ethylbenzene hydroperoxide. Since in actual practice water, when present, only partially enters into the reaction, the product is a mixture of 1-phenylethanol and acetophenone with the 1-phenylethanol predominating on a molar basis. Thus, the product distribution can be adjusted to some extent by controlling the water present in the reactor.

This reaction is carried out in the presence of a catalytic amount of osmium tetroxide using an organic polar solvent to ensure a homogeneous reaction since the osmium tetroxide is soluble in the polar solvent. Also present as a solvent is the unoxidized ethylbenzene present as the predominant component in the ethylbenzene hydroperoxide solution. The reaction solution is maintained strongly alkaline by the presence of a tetraalkylammonium hydroxide, which is soluble in the combined ethylbenzene polar solvent.

The polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbons, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 30 and about 98 weight percent of the reaction mixture, but will preferably comprise between about 50 and 80 percent of the reaction mixture.

The concentration of ethylbenzene hydroperoxide used in the reaction is not critical but will generally be from about one percent to about 20 weight percent of the reaction system preferably from about five percent to about 20 percent of the reaction mixture. The amount of ethylbenzene in the reaction system can vary between about 2.5 percent and about 50 weight percent but at preferred conditions of operation it will comprise between about ten and about 30 weight percent of the reaction mixture.

The gaseous olefin is incorporated into the reaction solution by pressuring the reactor. The pressure is not critical, rather it determines the amount that dissolves in the reaction solution. We find that a pressure between about 25 and about 1,500 psig. is useful with ethylene and between about 5 and about 150 psig. with propylene, however, we prefer to operate within a pressure range of between about 50 and about 150 psig. or between about 10 and about 50 psig, respectively.

The catalyst osmium tetroxide is used in catalytic quantities. We find that from 0.01 to ten mmols of the catalyst per 100 ml. of the reaction solution is suitable, however, we prefer to carry out the reaction using from about 0.03 to about 0.1 mmol of catalyst per 100 ml. of the reaction solution. The amount of catalyst can also be related to the amount of osmium metal that is used. Thus, about 50 to about 1,000 ppm. osmium can be used based on the total reaction solution in the reaction vessel, preferably about 100 to about 500 ppm. osmium. Also included in the term osmium tetroxide as used herein including the claims are osmium compounds which are converted to osmium tetroxide by ethylbenzene hydroperoxide including potassium osmate, sodium osmate, lithium osmate, and the like.

A small amount of a tetraalkylammonium hydroxide is also present in the reaction solution. This tetraalkylammonium hydroxide serves in this reaction system both as a base and as a phase transfer agent and as such it increases the solubility of the olefin in the reaction solution. Therefore, the tetraalkylammonium hydroxide aided by its basic properties serves to increase the reaction rate, increase the selectivity to desired products and improve the overall efficiency of the reaction.

The useful tetraalkylammonium hydroxides include those containing lower alkyl groups having from one to about five carbon atoms such as tetramethylammonium hydroxide, tetra-n-butylammonium hydroxide, and the like. This base is used in an amount between about 0.1 and about five weight percent of the reaction solution but it is preferred to use it within the range of about 0.2 to about two weight percent of the reaction solution, which amount provides a pH of about 14 in the solution. Since these bases are conventionally supplied in aqueous solution, the water for reaction if desired can be supplied by this solution. This water of reaction can be used in an amount up to about twenty weight percent of the reaction solution, but generally it is used in an amount between about one and about ten percent.

The second stage reaction is carried out at a moderate temperature. We find that a reaction temperature between about $-10°$ C. to about $30°$ C. is suitable but we prefer to operate within the range of about $-10°$ C. to about $25°$ C. It can be carried out as a batch reaction, as a continuous reaction or as a semi-continuous reaction. In the batch reaction all the necessary components are placed in a reaction vessel and the reaction is allowed to proceed for about one to about 24 hours for substantially complete reaction of the ethylbenzene hydroperoxide. In the continuous process the components can be introduced into the inlet of an elongated reactor at a rate that substantially complete reaction will have taken place by the time the reaction solution reaches the reactor outlet. The reaction can also be carried out in a semicontinuous manner by metering the reaction components into the first of one or more tank reactors in series.

The liquid reaction product contains 1-phenylethanol and acetophenone resulting from both the first stage oxidation reaction and the second stage decomposition reaction, ethylene or propylene glycol, the polar solvent, ethylbenzene, tetraalkylammonium hydroxide, osmium tetroxide and water, if added. Since the second stage reaction is generally and preferably carried to completion, there is no ethylbenzene hydroperoxide in the reaction product. Analysis of the reaction product does not reveal measurable amounts of oxidation products of the olefin other than the glycol. The volatile components are distilled out of the reaction mixture into various fractions leaving the osmium tetroxide and tetraalkylammonium hydroxide in the still. The glycol is separated from the high boiling distillate leaving a mixture of the 1-phenylethanol and acetophenone for further processing.

The mixture of 1-phenylethanol and acetophenone predominates in 1-phenylethanol generally in an amount between about 60 and 70 percent. This mixture is subjected to dehydration to convert the 1-phenylethanol to styrene. A suitable dehydration catalyst, preferably powdered and of high surface area, such as alumina, silica, titanium dioxide, titanium dioxide on alumina, titanium dioxide on silica, magnesia, and the like, is mixed with the liquid which is subjected to an elevated temperature, preferably between about $200°$ C. and about $300°$ C. When the conditions and catalyst are properly selected, a selectivity of 99 percent and yield of 95 percent to styrene can be accomplished. Product styrene is obtained by distillation from the reaction product. A mixture of acetophenone and unreacted 1-phenylethanol is separated from the catalyst and organic by-products and is hydrogenated to convert the acetophenone to 1-phenylethanol. Suitable hydrogenation catalysts include copper chromite, nickel or cobalt on kieselguhr, and the like, and the hydrogenation temperatures will generally range from about 150° to about 200° C. The resulting 1-phenylethanol can be added to the stream of 1-phenylethanol and acetophenone fed to the dehydration reactor.

DESCRIPTION OF PREFERRED EMBODIMENTS

In the following examples the ethylbenzene hydroperoxide was analyzed by iodometric titration. Product analysis for 1-phenylethanol and acetophenone was made by gas-liquid chromatographic analysis using a one-eighth inch I.D. by ten foot column of ten percent Carbowax on Chromosorb W by matching the peaks against authentic samples. Glycol analysis was carried out by gas chromatography and mass spectroscopic analysis.

EXAMPLE 1

The oxidation of ethylbenzene to produce ethylbenzene hydroperoxide was carried out in a 300 ml. glass reactor maintained in a constant temperature bath equipped with a magnetic stirrer, a gas bubbling tube and a dip tube for sampling. In the experiment 100 ml. of ethylbenzene, five ml. of 70 percent isobutane hydroperoxide and 0.1 percent (0.087 g.) of finely divided barium oxide catalyst were charged to the reactor. Air was then bubbled through the reaction mixture at a rate of 100 cc. per minute and a pressure of 140 psi. (965 kPa). The stirrer was started and the reactor was heated to 135° C. for three hours.

Iodometric titration of the reaction product disclosed 18.75 percent ethylbenzene hydroperoxide. Since most of the isobutane hydroperoxide initiator was decomposed during the reaction, the analysis for ethylbenzene hydroperoxide by iodometric titration included only a trace of isobutane hydroperoxide. The gas-liquid chromatograph analysis disclosed 78.89 percent ethylbenzene, 12.78 percent acetophenone, 5.58 percent 1-phenylethanol and 2.78 percent other products comprising primarily t-butanol from the decomposition of the isobutane hydroperoxide initiator. These analyses indicated a conversion of 21.1 percent and a selectivity to ethylbenzene hydroperoxide of 88.9 percent.

When pure ethylbenzene hydroperoxide was pyrolyzed in the gas-liquid chromatograph, the analysis showed 56 percent acetophenone, 21 percent 1-phenylethanol with the balance assumed to be oxygen and water which were not determined. With this data the selectivity to acetophenone and 1-phenylethanol was determined to be 5.7 percent and 5.4 percent, respectively.

EXAMPLE 2

The conditions, components and proportions of Example 1 were repeated except that barium oxide was omitted from the reaction vessel. Analysis of the product mixture showed a conversion of 13.7 percent and a concentration of 11.4 percent ethylbenzene hydroperoxide, 8.2 percent acetophenone and 6.0 percent 1-phenylethanol.

EXAMPLE 3

Ethylbenzene hydroperoxide was purified of 1-phenylethanol and acetophenone in order to accurately determine the amount of 1-phenylethanol and acetophenone that is produced in its decomposition. This was accomplished by extracting the ethylbenzene hydroperoxide with a 15 percent aqueous solution of sodium hydroxide and regenerating the sodium salt of the ethylbenzene hydroperoxide into a pure batch of ethylbenzene by acidification with bubbling carbon dioxide. This purified ethylbenzene hydroperoxide was by analysis determined to contain 26.5 percent ethylbenzene hydroperoxide, 0.5 percent 1-phenylethanol and a trace of acetophenone.

A charge of 100 ml. of t-butanol and 7.5 ml. of ten percent aqueous tetraethylammonium hydroxide was placed in a 300 ml. thick-walled glass reactor equipped with a thermocouple and a stirring magnet. The solution was cooled to 0° C. in an ice-salt bath. After adding 59 g. of the purified 26.5 percent ethylbenzene hydroperoxide to the chilled solution, the reactor was sealed. Ethylene was introduced into the reactor to a pressure of 120 psi. Then 5 ml. of 0.5 percent osmium tetroxide (0.1 mmol) in t-butanol was pressured into the reactor in a stream of ethylene. The pressure was adjusted to 150 psi. and the reaction was allowed to proceed for six hours at 0° C. and at 150 psi. (1.03 MPa). The reactor was then permitted to stand overnight at room temperature. Iodometric titration of this reaction solution gave zero percent ethylbenzene hydroperoxide. After evaporating the product, 100 ml. of ethanol were added to precipitate the inorganic portion. Analysis of the evaporated filtrate showed 3.57 g. of ethylene glycol (58 mmols), and a 98 percent selectivity of the ethylbenzene hydroperoxide to the mixture of 1-phenylethanol and acetophenone.

EXAMPLE 4

A sample of ethylbenzene hydroperoxide was purified as described in Example 3. The preceding experiment was duplicated except that 69 g. of the purified 26.5 percent ethylbenzene hydroperoxide solution (134 mmols ethylbenzene hydroperoxide) were used. The raw reaction product was analyzed by gas chromatograph and found to contain 132 mmols of combined 1-phenylethanol and acetophenone. This represents better than 98 percent selectivity and yield.

The reaction product was worked up using the same procedure as described in th preceding example. The high boiling fraction was separated and analyzed by gas chromatograph which had been calibrated using pure samples of 1-phenylethanol and acetophenone. This analysis showed 48 mmols of acetophenone and 87 mmols of 1-phenylethanol which corresponds to a product distribution of 35.5 mol percent acetophenone and 64.5 mol percent 1-phenylethanol.

EXAMPLE 5

The procedures, conditions and quantities of Example 3 were repeated except that unpurified 20 percent ethylbenzene hydroperoxide was used. The low boiling fraction in the evaporated filtrate following the precipitation of the inorganic portion was analyzed for two-carbon oxygenated derivatives of ethylene. A combination of gas chromatographic and mass spectrographic analysis disclosed none of the following in the product: acetaldehyde, acetic acid, ethanol, acetals of acetaldehyde, glycolaldehyde and glycolic acid. The sensitivity of this combined analysis was estimated to be about 0.5 weight percent of the total product.

EXAMPLE 6

An experiment was conducted using the same procedures, conditions and quantities of Example 5, except that the amount of ethylene involved in the reaction was carefully measured. The total amount of ethylene charged to the reactor, as measured by a calibrated rotameter, was 274 mmols. The ethylene vented at the conclusion of the reaction amounted to 210 mmols according to measurement in a wet-gas meter. The selectivity of ethylene to ethylene glycol based on 58 mmols of ethylene glycol and 64 mmols of unrecovered ethylene is 90 percent. But further analysis was carried out to account for possible handling losses of the gas. An identical blank test was run except that no ethylbenzene hydroperoxide and no catalyst were used. This resulted in a 95 percent recovery of ethylene. The five percent difference is believed to be the ethylene handling losses including ethylene dissolved in the solution. It was concluded that the selectivity of ethylene to ethylene glycol based on reacted ethylene is at least about 95 percent.

EXAMPLE 7

A charge of 100 ml. of t-butanol, 5 ml. of 0.5 percent osmium tetroxide (0.1 mmol) in t-butanol and 7.5 ml. of ten percent aqueous tetraethylammonium hydroxide was placed in a 300 ml. thick-walled glass reactor equipped with a thermocouple and a stirring magnet. The solution was cooled to 0° C. in an ice-salt bath. After adding 59 g of 20 percent ethylbenzene hydroperoxide (80 mmols) to the chilled solution, the reactor was sealed. Propylene (10 g.) was introduced into the reactor from a charge tube. The temperature inside the reactor rose to 13° C. and the pressure rose to about 80 psi. In about 20 minutes the reactor temperature returned to 0° C. and the reaction was allowed to proceed for six hours at 0° C. The reactor was then permitted to stand overnight at room temperature. After evaporating the product, 100 ml. of ethanol were added to precipitate the inorganic portion. Analysis of the evaporated filtrate showed a 98 percent selectivity of the ethylbenzene hydroperoxide to 1-phenylethanol and acetophenone. The analysis also showed 3.39 g. of propylene glycol (44.6 mmols) which represented a yield of 58 percent based on the ethylbenzene hydroperoxide and a selectivity of 95 percent based on reacted olefin.

EXAMPLE 8

A 14 g. (100 mmols) sample of 1-decene, 200 ml. of t-butanol and 15 ml. of ten percent aqueous tetraethylammonium hydroxide were added to a 500 ml. round bottom flask. The flask and contents were cooled to 0° C. in a sodium chloride ice bath. After reaching temperature, 113 g. of 20 percent (160 mmols) ethylbenzene hydroperoxide and 10 ml. of 0.5 percent osmium tetroxide in t-butanol were added. The reaction was allowed to proceed for about 15 hours. Analysis after product recovery showed that the reaction with ethylbenzene hydroperoxide had formed 4.32 g. (24.8 mmols) of 1,2-dihydroxydecane, a 15.5 percent yield based on the ethylbenzene hydroperoxide. It was also determined that the 1-decene had completely reacted at a selectivity of 24.8 percent glycol based on 1-decene reacted. This experiment demonstrates that the method of Example 5 is not useful for diol production with higher alpha-olefins.

EXAMPLE 9

A 100 g. solution containing 33 percent acetophenone and 67 percent 1-phenylethanol, recovered as the bottoms after the distillative separation from ethylbenzene and ethylene glycol, is converted to styrene. The solution is mixed with 32 g. of 1-phenylethanol obtained from the hydrogenation of acetophenone. To this mixture is added 26 g. of powdered alumina and it is heated to 265° C. After five hours, the reaction product is separated into an aqueous fraction and an organic fraction. The organic fraction is distilled into 93.1 g. of styrene. The conversion of 1-phenylethanol is 96 percent and the selectivity to styrene is 98 percent. The acetophenone containing unreacted 1-phenylethanol is hydrogenated over a copper chromate catalyst at 150° C. and this hydrogenation product is recycled and dehydrated as described.

The reaction of ethylbenzene hydroperoxide with the olefin is preferably carried out with a stoichiometric excess, more preferably at least a 25 percent excess, of the olefin to substantially completely react all of the ethylbenzene hydroperoxide. If unreacted ethylbenzene hydroperoxide shows up in the reaction product, it is removed in an extra processing step to avoid undesired decomposition during product work-up. Therefore, insuring the substantial absence of the hydroperoxide in the reaction product is a safety procedure and avoids extra processing costs. Additionally, we believe that this substantial absence of undesired oxidation by-products of the olefin is, at least in part, a result of the use of a stoichiometric excess of the olefin during the second stage reaction.

It is to be understood that the above disclosure is by way of specific example and that numerous modifications and variations are available to those of ordinary skill in the art without departing from the true spirit and scope of the invention.

We claim:

1. A method of converting ethylbenzene to styrene at high selectivity which comprises the steps
   a. contacting ethylbenzene at an elevated temperature under substantially anhydrous conditions with molecular oxygen whereby an oxidized solution containing ethylbenzene hydroperoxide, 1-phenylethanol and acetophenone in ethylbenzene is obtained,
   b. contacting said oxidized solution with ethylene or propylene at an elevated pressure in an organic polar solvent and in the presence of a tetraalkylammonium hydroxide and osmium tetroxide at a moderate temperature whereby 1-phenylethanol and acetophenone are produced, and
   c. separating out a mixture of the 1-phenylethanol and acetophenone obtained in steps a and b from the reaction mixture and hydrogenating the acetophenone to 1-phenylethanol and dehydrating the 1-phenylethanol to styrene.

2. A method of converting ethylbenzene to styrene at high selectivity in accordance with claim 1 in which the solution in step b contains up to about twenty weight percent water.

3. A method of converting ethylbenzene to styrene at high selectivity in accordance with claim 2 in which the ethylbenzene is contacted with molecular oxygen in the presence of anhydrous, powdered barium oxide.

4. A method of converting ethylbenzene to styrene at high selectivity in accordance with claim 2 in which the solution of ethylbenzene hydroperoxide and ethylbenzene contains between about 5 and about 50 weight percent ethylbenzene hydroperoxide.

5. A method of converting ethylbenzene to styrene at high selectivity in accordance with claim 2 in which the tetraalkylammonium hydroxide is between about 0.1 and 5 weight percent of the total solution.

6. A method of converting ethylbenzene to styrene at high selectivitity in accordance with claim 5 in which the solution contains between about 0.01 and about 10 mmols of osmium tetroxide per 100 ml. of solution.

7. A method of converting ethylbenzene to styrene at high selectivity in accordance with claim 2 in which the polar solvent is selected from aliphatic alcohols, ketones and ethers having up to about six carbon atoms.

8. A method of converting ethylbenzene to styrene at high selectivity in accordance with claim 2 in which said elevated temperature is between about 120° C. and about 150° C.

9. A method of converting ethylbenzene to stryene at high selectivity in accordance with claim 2 in which said moderate temperature is between about −10° C. and about 30° C.

10. A method of converting ethylbenzene to styrene at high selectivity in accordance with claim 2 in which the tetraalkylammonium hydroxide is tetraethylammonium hydroxide, tetrapropylammonium hydroxide or tetrabutylammonium hydroxide.

11. A method of converting ethylbenzene to styrene at high selectivity in accordance with claim 2 in the presence of between about 0.01 and about ten mmols of osmium tetroxide per 100 ml. of the reaction solution.

12. A method of converting ethylbenzene to styrene at high selectivity in accordance with claim 2 in which the said elevated pressure is between about 10 and about 150 psig.

13. A method of converting ethylbenzene to styrene at high selectivity in accordance with claim 2 in which there is at least about a 25 percent stoichiometric excess of the olefin.

* * * * *